United States Patent

Berg et al.

[11] 4,048,326
[45] Sept. 13, 1977

[54] TREATMENT OF HELMINTH INFECTIONS WITH SUBSTITUTED 1,2-BIS(THIOUREIDO)BENZENE

[75] Inventors: Samuel Sidney Berg, Ilford; David Conwil Jenkins, Gidea Park; Ronald Frederick Phillipson, Brentwood, all of England

[73] Assignee: May & Baker Limited, England

[21] Appl. No.: 153,409

[22] Filed: June 15, 1971

[30] Foreign Application Priority Data

| June 16, 1970 | United Kingdom | 29529/70 |
| June 22, 1970 | United Kingdom | 30244/70 |
| Sept. 4, 1970 | United Kingdom | 42609/70 |
| Mar. 31, 1971 | United Kingdom | 8292/71 |
| June 11, 1971 | France | 71.21293 |

[51] Int. Cl.² ............................................. A61K 31/27
[52] U.S. Cl. ....................................... 424/300; 560/16
[58] Field of Search ......................... 424/300; 260/470

[56] References Cited

U.S. PATENT DOCUMENTS 3,810,992   5/1974   Menn .................................. 424/300

FOREIGN PATENT DOCUMENTS 1,191,406   5/1970   United Kingdom ................. 260/470

Primary Examiner—V. D. Turner
Attorney, Agent, or Firm—Stevens, Davis, Miller & Mosher

[57] ABSTRACT

Benzene derivative of the formula:

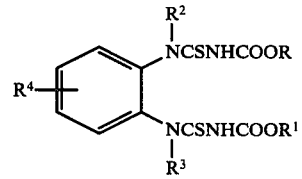

wherein R and $R^1$ each represent an aliphatic hydrocarbon group optionally substituted by halogen or alkoxy, $R^2$ and $R^3$ each represent hydrogen or methyl, and $R^4$ represents hydrogen, halogen, alkyl, alkanoylamino optionally substituted by cycloalkyl of 3 to 6 carbon atoms, alkoxycarbonylamino, alkanoyl, benzyl or N-methylmethanesulphonylamino, possess anthelmintic and anti-viral activity. New compounds within that formula also possess fungicidal properties.

15 Claims, No Drawings

TREATMENT OF HELMINTH INFECTIONS WITH SUBSTITUTED 1,2-BIS(THIOUREIDO)BENZENE

This invention relates to benzene derivatives, compositions containing them and their use as anthelmintics, agricultural pesticides and anti-viral agents.

As a result of research and experimentation, it has been found that the benzene derivatives of the general formula:

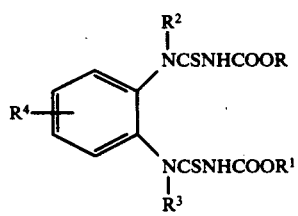

(wherein R and $R^1$ each represent a straight- or branched-chain aliphatic hydrocarbon group containing not more than 4 carbon atoms which may be saturated or unsaturated, e.g. allyl or propargyl, and which may optionally be substituted by a halogen atom, e.g. chlorine, or an alkoxy group containing not more than 4 carbon atoms, $R^2$ and $R^3$ each represent a hydrogen atom or a methyl group, and $R^4$ represents a hydrogen or a halogen atom, e.g. chlorine or fluorine, or a straight- or branched-chain alkyl group containing not more than 4 carbon atoms, an alkanoylamino group containing 1 to 4 carbon atoms in which the alkanoyl moiety may be straight- or branched-chain and may optionally be substituted by a cycloalkyl group containing from 3 to 6 carbon atoms, e.g. acetamido, cyclopropylcarbonamido or cyclohexylacetamido, an alkoxycarbonylamino group containing from 2 to 4 carbon atoms in which the alkoxy moiety may be straight-or branched-chain, a straight-or branched-chain alkanoyl group containing from 2 to 4 carbon atoms, a benzoyl group or a group $CH_3SO_2N(CH_3)_3$—) possess valuable chemotherapeutic properties, having, in particular, high anthelmintic and anti-viral activity.

When the compounds of general formula I can exist in stereoisomeric forms, all such isomers and their mixtures and racemates are included within the scope of the present invention.

According to a feature of the present invention, there is provided a method for the treatment of helminth infections in men and domestic animals, for example cattle, sheep, pigs, goats, poultry and equines, for example infections of the gastro-intestinal tract caused by parasitic nematode worms, for example members of the family Trichostrongylidae, in domestic animals which comprises the administration of an anthelmintically effective amount of one or more compounds of general formula I.

The quantities of the compounds of formula I administered in the treatment of helminthiasis will vary with the species of animal treated, the nature and severity of the infection, the length of treatment and the method of administration. In general, the compounds are effective in treating helminthiasis when administered orally to domestic animals in dosage which may be as low as 5mg/kg of animal body weight but which are preferably from about 25 mg/kg to about 250 mg/kg of animal body weight. Higher doses up to 500 mg/kg of animal body weight or even as high as 1000 mg/kg of animal body weight may, however, be used.

The quantities referred to above of the compounds of general formula I may be administered on one or more occasions or divided into a number of smaller doses and administered over a period.

The value of the compounds of formula I as anthelmintics has, for example, been demonstrated in the following tests:

A. Activity against roundworms in rats

Test 1 — Rats were infected with 100 Nippostrongylus brasiliensis larvae each, by the subcutaneous route. After 6 days, when the infection was patent, the rats were randomised and allotted to groups of 10 animals each, ready for treatment. One group was used for each dose level of the test compound and, in each experiment, one group was left untreated as a control. All the rats were killed for post-mortem worm counts 48 hours after treatment. The activity, expressed in terms of the percentage reduction in mean worm load of the treated group compared with the untreated group, is shown in Table I.

Test 2 — Rats were infected with 100 Nippostrongylus brasiliensis larvae each, by the subcutaneous route. After 24 hours the rats were randomised and allotted to groups of 5 animals each, ready for treatment. Doses of the test compound were then administered to each group by the oral, subcutaneous and intraperitoneal routes respectively, one group of 10 animals being left untreated as a control. All the rats were killed for post-mortem worm counts 6 days after dosing. The activities, expressed in terms of the percentage reductions in mean worm load of the treated groups or damage to the worms compared with the untreated control group, are given below in Table I.

TABLE I

| Test Compound | Test | Dose (mg/kg animal body weight) | Route of Administration | Percentage reduction in N. brasiliensis load or worm damage |
|---|---|---|---|---|
| 1,2-bis-(3-methoxycarbonyl-2-thioureido)-benzene | 1 | 1000 | oral | 99 |
| | 1 | 500 | oral | 87 |
| | 1 | 250 | oral | 83 |
| | 1 | 125 | oral | 41.5 |
| | 2 | 1000 | oral | 99 |
| 1,2-bis-(3-ethoxycarbonyl-2-thioureido)-benzene | 1 | 1000 | oral | worm damage |
| | 2 | 1000 | oral | 99 |
| 1,2-bis-(3-methoxycarbonyl-2-thioureido)-4-n-butylbenzene | 2 | 1000 | oral | worm damage |
| 1-(3-methoxycarbonyl-2-thioureido)-2-(3-ethoxycarbonyl-2-thioureido)benzene | 1 | 500 | oral | 67 |
| 1,2-bis(3-methoxycarbonyl-2-thioureido)-4-acetamidobenzene | 2 | 1000 | oral | 38 and worm damage |
| 1,2-bis-(3-allyloxycarbonyl-2-thioureido)benzene | 2 | 1000 | oral | 97.2 |
| 1,2-bis-(3-methoxycarbonyl-2-thioureido)-4-fluoro-benzene | 1 | 1000 | oral | worm damage |
| | 2 | 1000 | oral | 91 and worm damage |
| 3,4-bis-(3-methoxycarbonyl-2-thioureido)benzophenone | 2 | 1000 | oral | 63 and worm damage |

B. Activity against roundworms in mice

Mice were infected with approximately 100 *Trichinella spiralis* larvae each, by the oral route. The mice were randomised and allotted to groups of 4 animals each ready for treatment. Doses of the test compound were then administered to each group by the oral or subcutaneous routes at 2 hours post infection and again at 24 hours post infection, one group of 4 animals being left untreated as a control. All the mice were killed for postmortem examination 5 days after the second dose. The activity, expressed in terms of the percentage reduction in mean worm load of the treated group compared with the control group, is shown in Table II.

TABLE II

| Test Compound | Dose (mg/kg animal body weight) | Route of Administration | Percentage reduction in T. *spiralis* worm load |
|---|---|---|---|
| 1,2-bis-(3-methoxycarbonyl-2-thioureido)benzene | 2 × 500 | oral | 100 |
| 1,2-bis-(3-ethoxycarbonyl-2-thioureido)benzene | 2 × 500 | oral | 100 |

C. Activity against roundworms in sheep a. Activity against *Haemonchus contortus, Trichostrongylus colubriformis, Nematodirus battus* and *Ostertagia circumcincta* in their 4th larval and adult stages in lambs i. 12 worm-free lambs were each infested with 3,000 H. contortus, 15,000 T. colubriformis and 8,300 N. battus larvae by the oral route. After 7 days, 2 animals were treated orally with 200 mg/kg animal body weight of 1,2-bis-(3-methoxycarbonyl-2-thioureido)benzene and 2 with 1,2-bis-(3-ethoxycarbonyl-2-thioureido) benzene to examine the effects against the 4th larval stages of the worms. 23 Days after infection, 2 more animals were treated with 50 mg/kg animal body weight of each test compound, to examine the effects against mature adult worms. 28 Days after infection, all animals were killed for post-mortem worm counts and the burdens of each worm species in the 8 treated animals compared with those in the remaining 4 control animals. The results are shown hereinafter in Table III.

ii. 12 worm-free lambs were each infected with 2,000 H. contortus 20,000 T. colubriformis and 15,000 O. circumcincta larvae by the oral route. After 7 days, 2 animals were treated orally with 50 mg/kg animal body weight, and 2 with 25 mg/kg animal body weight, of 1,2-bis-(3-ethoxycarbonyl-2-thioureido)benzene. 23 days after infection similar doses were administered to another 4 animals. 28 Days after infection, all animals were killed for post-mortem worm counts and the results evaluated as in experiment (a)(i). These results are shown hereinafter in Table IV.

TABLE III

| Compound | Stage | Mean percentage reduction in worm burdens | | |
|---|---|---|---|---|
| | | H. *contortus* | T. *colubriformis* | N. *battus* |
| 1,2-bis-(3-methoxycarbonyl-2-thioureido)benzene | 4th larval | 99.0 | 99.9 | 100 |
| | Adult | 100 | 99.8 | 85.6 |
| 1,2-bis-(3-ethoxycarbonyl-2-thioureido)benzene | 4th larval | 100 | 100 | 100 |
| | Adult | 100 | 99.5 | 75.9 |

TABLE IV

| Dose level (mg/kg animal body weight) | Stage | Mean percentage reduction in worm burdens | | |
|---|---|---|---|---|
| | | H. *contortus* | T. *colubriformis* | O. *circumcincta* |
| 50 | 4th larval | 100 | 99.9 | 98.0 |
| 50 | Adult | 98.2 | 100 | 99.9 |
| 25 | 4th larval | 81.5 | 99.8 | 80.9 |
| 25 | Adult | 99.1 | 99.9 | 97.1 | b. Activity against *Haemonchus contortus, Trichostrongylus axei* and *Trichostrongylus colubriformis* in their 4th larval and adult stages in lambs i. 7 worm-free lambs were each infected with H. contortus (approximately 9,000), T. axei (approximately 7,000) and T. colubriformis (approximately 12,000) infective larvae. After 7 days, 2 lambs were treated orally with 100 mg/kg animal body weight of 1,2-bis-(3-methoxycarbonyl-2-thioureido)-4-n-butylbenzene against the 4th larval stages of the worms. 23 days after infection, all 7 lambs were killed for post-mortem worm counts and the burdens of each worm species in the 2 treated animals compared with those in the remaining 5 untreated control animals. The mean percentage reduction in worm burdens were found to be 97.5%, 73.3% and 85.2% for H. contortus, T. axei and T. colubriformis respectively.

ii. 6 worm-free lambs were each infected with H. contortus (approximately 5,600), T. axei (approximately 9,300) and T. colubriformis (approximately 10,000) infective larvae. After 22 days, 2 lambs were treated orally with 15 mg/kg animal body weight of 2,3-bis-(3-methoxycarbonyl-2-thioureido)toluene against the mature adult stages of the worms. 27 days after infection, all 6 lambs were killed for post-mortem worm counts and the burden of each worm species in the 2 treated animals compared with those in the remaining 4 untreated control animals. The mean percentage reduction in worm burdens were found to be 68.7, 83.8 and 32.8% for H. contortus, T. axei and T. colubriformis, respectively.

c. Effect on faecal egg output in naturally infected sheep (ewes and lambs)

Faecal material from sheet with naturally acquired strongyle infections was incubated for 7 days at 27° C. followed by identification of the infective larvae present. Amongst those species present were O. circumcincta, H. contortus and Cooperia spp. Most lambs also carried Nematodirus spp.

Egg counts were carried out on individual samples of faeces taken from the animals two and one day previous to dosings.

Similar counts were carried out immediately after dosing and at intervals until three weeks after dosing, the animals having been randomised into comparable groups on the basis of the egg counts determined before dosing.

Egg counts were made using the McMaster technique. If a count by this technique was negative, a positive/negative egg flotation determination was made.

i. Ewes

Groups of 3 ewes were treated orally with 50 mg/kg animal body weight of test compound and further egg counts made at intervals for 3 weeks after treatment. The results are shown hereinafter in Table V.

ii. Lambs

Groups of 7 lambs were treated orally with either 12.5, 25 or 50 mg/kg animal body weight of either 1,2-bis-(3-methoxycarbonyl-2-thioureido)benzene or 1,2-bis-(3-ethoxycarbonyl-2-thioureido)-benzene. Faecal egg counts were then made 48 hours, 7 days, 14 days and 21 days after treatment. Samples were also taken from 21 untreated lambs. The figures hereinafter shown in Table VI are the number of faecal samples with more than 50 eggs per gm. faeces/number of faecal samples examined.

TABLE V

| | Mean faecal egg count/gm. faeces | | | | | | | | | | | |
|---|---|---|---|---|---|---|---|---|---|---|---|---|
| | Days before treatment with drug | | Treatment day | Days after treatment with drug | | | | | | | | |
| Compound | 2 | 1 | | 1 | 4 | 6 | 8 | 11 | 15 | 18 | 20 | 22 |
| 1,2-bis-(3-methoxycarbonyl-2-thioureido)benzene | 350 | 500 | 934 | 1017 | 0 | <50 | <50 | <50 | <50 | <50 | <50 | <50 |
| 1,2-bis-(3-ethoxycarbonyl-2-thioureido)benzene | 350 | 583 | 325 | 300 | 0 | 0 | 0 | 0 | 0 | 0 | 0 | 0 |

TABLE VI

| | | TIME AFTER TREATMENT | | | | | | | |
|---|---|---|---|---|---|---|---|---|---|
| | | 48 hours | | 7 days | | 14 days | | 21 days | |
| Compound | Dose mg/kg | Nematodirus | others | Nematodirus | others | Nematodirus | others | Nematodirus | others |
| 1,2-bis-(3-methoxycarbonyl-2-thioureido)benzene | 50 | 0/3 | 0/3 | 0/5 | 0/5 | 0/6 | 0/6 | 0/7 | 0/7 |
| | 25 | 3/4 | 0/4 | 3/4 | 0/4 | 3/6 | 3/6 | 6/7 | 3/7 |
| | 12.5 | 1/3 | 0/3 | 5/7 | 2/7 | 2/5 | 1/5 | 3/5 | 0/5 |
| 1,2-bis-(3-ethoxycarbonyl-2-thioureido)benzene | 50 | 0/4 | 0/4 | 0/6 | 0/6 | 0/5 | 0/5 | 0/6 | 0/6 |
| | 25 | 0/4 | 0/4 | 2/5 | 2/5 | 3/7 | 5/7 | 2/6 | 4/6 |
| | 12.5 | 1/3 | 1/3 | 4/5 | 3/5 | 6/7 | 7/7 | 5/7 | 7/7 |
| Control | 0 | 12/13 | 13/13 | 15/21 | 21/21 | 10/18 | 18/18 | 9/20 | 20/20 |

D. In vitro activity against roundworms

Compounds of formula I were tested at concentrations of 100 μg/ml, 10 μg/ml, 1 μg/ml and 0.1 μg/ml in small glass containers. If the compound was not soluble in water, a volatile organic medium, e.g. acetone, chloroform, ethanol or methanol, was used. An amount of material appropriate for each final concentration was measured and placed in duplicate test containers and if an organic solvent was used it was allowed to evaporate completely.

Nippostrongylus brasiliensis eggs were recovered by saturated saline centrifugal flotation from the faeces of rats heavily infected with third stage larvae six days previously. They were washed several times in water and suspended in water in a suitable concentration. From 25–50 eggs were placed in each container and the final volume was made up by the addition of a very dilute aqueous suspension of mouse faeces which served as the growth medium.

The minimum inhibitory concentrations of each compound (M.I.C.) shown in the following Table VII was the minimum concentration in μg/ml total liquid volume at which it inhibited or delayed hatching of eggs, or at which it killed, retarded growth or reduced activity of larvae during the 4 days after beginning the test.

TABLE VII

| COMPOUND | M.I.C. (μg/ml) |
|---|---|
| 1,2-bis-(3-methoxycarbonyl-2-thioureido)benzene | 1.0 |
| 1,2-bis-(3-ethoxycarbonyl-2-thioureido)benzene | 1.0 |
| 1,2-bis-(3-methoxycarbonyl-2-thioureido)-4-n-butylbenzene | 0.1 |
| 1,2-bis-(3-ethoxycarbonyl-2-thioureido)-4-n-butylbenzene | 0.1 |

TABLE VII-continued

| COMPOUND | M.I.C. (μg/ml) |
|---|---|
| 2,3-bis-(3-methoxycarbonyl-2-thioureido)toluene | 0.1 |
| 3,4-bis-(3-methoxycarbonyl-2-thioureido)toluene | 1.0 |
| 1,2-bis-(3-methoxycarbonyl-2-thioureido)-4-isopropoxycarbonylaminobenzene | 100.0 |
| 1,2-bis-(3-ethoxycarbonyl-2-thioureido)-4-chlorobenzene | 10.0 |
| 1-(3-methoxycarbonyl-2-thioureido)-2-(3-ethoxycarbonyl-2-thioureido)benzene | 1.0 |
| 1,2-bis-(3-isopropoxycarbonyl-2-thioureido)benzene | 0.1 |
| 1,2-bis-(3-methoxycarbonyl-2-thioureido)-4-acetamidobenzene | 100.0 |
| 1-(3-ethoxycarbonyl-2-thioureido)-2-(3-ethoxycarbonyl-1-methyl-2-thioureido)benzene | 10.0 |
| 1,2-bis-(3-allyloxycarbonyl-2-thioureido)benzene | 0.1 |
| 1,2-bis-(3-methoxycarbonyl-2-thioureido)-4-fluorobenzene | 1.0 |
| 1,2-bis-(3-ethoxycarbonyl-2-thioureido)-4-fluorobenzene | 1.0 |
| 1,2-bis-(3-propargyloxycarbonyl-2-thioureido)benzene | 1.0 |
| 3,4-bis-(3-methoxycarbonyl-2-thioureido)acetophenone | 10.0 |
| 3,4-bis-(3-methoxycarbonyl-2-thioureido)benzophenone | 0.1 |

E. Activity against tapeworms

A suspension of Hymenolepis nana embryophores was prepared by grinding adult worms (taken from the small intestines of mice infected three weeks previously) in physiological saline in a mortar. The suspension was filtered and the number of embryophores counted.

Mice were infected by oral admistration of 1 ml of this suspension containing 1000 mature embryophores.

After 21 days, where the infection was patent, the mice were treated with a single oral administration of the test compound. 3 days after this treatment the mice, fasting since the night before, were killed, and the worms present in the small intestine were counted.

The dose of the compound which rendered 50% of the mice completely free of parasites was calculated.

The results are summarised in Table VIII

TABLE VIII

| Test Compound | Oral Dose mg/kg | No. of mice treated | No. of mice cured | *CD$_{50}$ mg/kg p.o. |
|---|---|---|---|---|
| 1,2-bis-(3-methoxycarbonyl-2-thio- | 0 | 10 | 0 | |
| | 100 | 6 | 0 | |

TABLE VIII-continued

| Test Compound | Oral Dose mg/kg | No. of mice treated | No. of mice cured | *CD$_{50}$ mg/kg p.o. |
|---|---|---|---|---|
| ureido)benzene | 250 | 6 | 1 | 380 |
|  | 500 | 6 | 5 |  |

*CD$_{50}$ = Median curative dose

The compounds of general formula I also possess valuable anti-viral activity, for example against the myxovirus A$_2$/Hong Kong/5/68 which causes influenza in man. The quantities of the compounds of formula I administered in the treatment of viral infections will vary with the species of animal treated, the nature and severity of the infection, the length of treatment and the method of administration. In general, the compounds are effective in treating viral infections, more particularly infections of virus A$_2$/Hong Kong/5/68, when administered orally at dosages between 50 and 250 mg/kg of animal body weight. The quantities may be administered on one or more occasions or divided into a number of smaller dosages and administered over a period.

The anti-viral activity of the compounds of general formula I has, for example, been demonstrated in the following test:

Two groups of five mice, each weighing approximately 20 g., were dosed with 1,2-bis-(3-allyloxycarbonyl-2-thioureido)-benzene and with 1,2-bis-(3-ethoxycarbonyl-2-thioureido)-4-chlorobenzene at a rate of 250 mg/kg animal body weight by oral administration. Three hours later each animal was infected by intranasal inoculation with 0.02 ml. of a 10$^{-1}$ dilution of a suspension of lung tissue, disintegrated by ultrasonic vibration, from mice infected with influenza virus type A$_2$/Hong Kong/5/68. One hour after infection, the animals were again dosed orally with the test compound at the same rate of administration. Twenty four hours after infection, the mice were killed, the lungs removed and those from the five animals which had received the same test compound were pooled and disintegrated by ultrasonic vibration in phosphate-buffered saline to give a 10% w/v suspension. After incubation for one hour at 37° C. and centrifugation, the supernatant fluid was removed and serially diluted from a concentration of 1/2 to 1/8192. The viral content was then determined by the addition of a 0.5% w/v suspension of chicken blood red cells to determine the greatest dilution of supernatant fluid which produced agglutination of the chicken blood red cells (the haemagglutinin titre) and compared with the corresponding haemagglutinin titre obtained from similarly-infected, untreated, groups of control animals. The haemagglutin titre with the mice treated with 1,2-bis-(3-allyloxycarbonyl-2-thioureido)-benzene was ⅛ and with the control animals was 1/2048, and the haemagglutinin titre with the mice treated with 1,2-bis-(3-ethoxycarbonyl-2-thioureido)-4-chlorobenzene was 1/128 and with the control animals 1/4096.

The compounds of general formula I are conveniently administered as anthelmintics and anti-viral agents in the form of compositions in a unit dosage form, and the present invention includes within its scope therapeutically-useful, more especially veterinary, compositions which comprise, as active ingredient, at least one benzene derivative of formula I in association with a significant amount of a pharmaceutically acceptable carrier or coating. The invention includes especially such compositions made up for oral administration, for example a tablet, pill, capsule or bolus, or more particularly, a paste, gel or drench.

Solid compositions for oral administration include compressed tablets, pills, boluses and granules, which may optionally be coated with a pharmaceutically acceptable alkali-stable or acid-stable material (e.g. an enteric coating) and dispersible powders. In such solid compositions one or more of the active compounds is or are admixed with at least one inert diluent such as potato starch, alginic acid, sucrose, lactose, or a resin. The compositions may also comprise, as is normal practice, additional substances other than inert diluents, e.g. lubricating agents such as magnesium stearate. Semi-solid compositions for oral administration include pastes and gels containing the active substance and a suitable inert diluent such as polyethylene glycol (6000). Liquid compositions for oral administration include pharmaceutically acceptable emulsions, solutions, suspensions, syrups and elixirs containing inert diluents commonly used in the art, such as water and liquid paraffin. Besides inert diluents such compositions may also comprise compatible adjuvants such as wetting, suspending and emulsifying agents and stabilising, thickening, perfuming, sweetening and flavouring agents. The compositions according to the invention for oral administration also include capsules of absorbable material such as gelatin containing one or more of the active substances with or without the addition of diluents or excipients.

Preparations according to the invention for parenteral administration include sterile aqueous, aqueous-organic and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilising, preserving, wetting, emulsifying and dispersing agents. They may be sterilised, for example, by filtration through a bacteria-retaining filter, by incorporation in the compositions of sterilising agents, or by heating. They may also be manufactured in the form of sterile solid compositions, which can be dissolved in sterile water or some other sterile injectable medium immediately before use.

The percentage of the benzene derivatives of formula I in the above compositions may be varied, it being necessary that it should constitute a proportion such that a suitable dosage for the therapeutic effect desired shall be obtained. In general, compositions containing from about 5% to about 90% by weight of active ingredient are satisfactory.

For therapeutic purposes, particularly when continuous administration over a period is desired, the compounds of general formula I may be administered dispersed in, or mixed with, animal feedstuffs, drinking water and other liquids normally consumed by the animals, or in compositions containing the benzene derivatives dispersed in or mixed with any other suitable inert physiologically innocuous carrier or diluent which is orally administrable. By the term 'inert physiologically innocuous carrier or diluent' is meant a carrier or diluent which is substantially non-reactive with the active ingredient and is not harmful to the animals on oral administration. Such compositions may be administered in the form of powders, pellets, solutions, suspensions and emulsions, to the animals to supply the desired dosage of the benzene derivatives or used as concentrates or supplements to be diluted with additional carrier, feedstuff, drinking water or other liquids normally consumed by the animals, before administration. Suitable inert physiologically innocuous carriers or diluents include wheat flour or meal, maize gluten, lactose, glucose, sucrose, talc, kaolin, calcium phosphate, potassium sulphate and diatomaceous earths such as keiselguhr. Concentrates or supplements intended for incorporation into drinking water or other liquids normally consumed by the animals to give solutions, emulsions or stable suspensions, may also comprise the active ingredient in association with a surface-active wetting, dispersing or emulsifying agent such as Teepol, polyoxyethylene(20)sorbitan mono-oleate or the condensation product of β-naphthalenesulphonic acid with formaldehyde, with or without a physiologically innocuous, preferably water-soluble, carrier or diluent, for example, sucrose, glucose or an inorganic salt such as potassium sulphate, or concentrates or supplements in the form of stable dispersions or solutions obtained by mixing the aforesaid concentrates or supplements with water or some other suitable physiologically innocuous inert liquid carrier or diluent, or mixtures thereof.

The compositions described above may be prepared by mixing the benzene derivatives of formula I with the inert physiologically innocuous carriers or diluents in any manner known to the art. Solid compositions are conveniently prepared by intimately mixing or dispersing the benzene derivatives uniformly throughout the feedstuffs or other solid carrier or diluent by methods such as grinding, stirring, milling or tumbling or by dissolving the benzene derivatives in a solvent, e.g. water or a suitable organic solvent, dispersing the solution so obtained in the feedstuff or other solid carrier or diluent and removing the solvent by any means known to the art. Medicated feedstuffs may also be prepared by mixing in concentrates or supplements containing higher concentrates of active ingredient to give feedstuffs throughout which the benzene derivatives are uniformly distributed at the desired concentration. The desired concentration of active ingredient in the compositions of the present invention is obtained by the selection of an appropriate ratio of the benzene derivatives to carrier or diluent.

Medicated feedstuffs will normally contain between 0.001% and 3% by weight of the benzene derivatives of formula I to give the required dosage. Concentrates and supplements will normally contain between 5% and 90%, preferably 5% to 50%, by weight of the benzene derivatives being, if desired, suitably diluted as hereinbefore described to give the required dosage.

Medicated animal feedstuffs, drinking water and other liquids normally consumed by the animals and compositions containing the benzene derivatives of formula I dispersed in, or admixed with, any other suitable inert carrier or diluent, as hereinbefore described, including concentrates or supplements, form further features of the present invention.

Compositions according to the present invention may also contain bacteriostats, bactericidal agents, sporicidal agents and pharmaceutically-acceptable colouring agents. The compositions may also contain, if desired, auxiliary therapeutic agents, for example fluke drugs such as 4-cyano-2-iodo-6-nitrophenol, hexachloroethane, carbon tetrachloride, 3,3', 5,5', 6,6'-hexachloro-2,2'-dihydroxydiphenylmethane, 2,2'-dihydroxy-3,3',5,5',6-pentachlorobenzanilide, 2,2'-dihydroxy-3,3'-dinitro-5,5'-dichlorodiphenyl or 2-acetoxy-4'-chloro-3,5-diiodobenzanilide, 2-(4-thiazolyl)benzimidazole, 5(6)-isopropoxycarbonylamino-2-(4-thiazolyl)benzimidazole, methyl 5(6)-butyl-2-benzimidazolecarbamate, methyl 5(6)-benzoyl-2-benzimidazolecarbamate, 6-phenyl-2,3,5,6-tetrahydroimidazo[2,1-b]-thiazole, trans-1,4,5,6-tetrahydro-1-methyl-2-(2-thiene-2'-ylvinyl)-pyrimidine, phenothiazine, cyanacethydrazide, piperazine and its salts such as piperazine adipate, 1-diethylcarbamoyl-4-methylpiperazine, tetrachloroethylene, 4,4'-dichloro-2,2'-dihydroxydiphenylmethane, N-(2-chloro-4-nitrophenyl)-5-chlorosalicylamide, N,N-dibutyl-4-hexyloxynaphthamidine, trans-1,4-bis-(2-isothiocyanatoethyl)cyclohexane and 1-styrylpyridinium salts, e.g. the bromide, embonate, amsonate or isethionate.

Compounds of general formula I may be prepared by the suitable adaptation of known methods, for example:

1. by the reaction of an isothiocyanate of the general formula:

$$SCNCO_2R \qquad\qquad II$$

(wherein R is as hereinbefore defined) with an amine of the general formula:

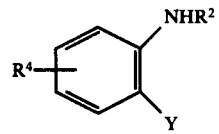

III wherein Y represents a group

$R^1$ and $R^3$ being as hereinbefore defined, or a primary amino or monomethylamino group, and $R^2$ and $R^4$ are as hereinbefore defined. The reaction may be carried out in the presence of an inert solvent, for example a lower alkanone, e.g. acetone or methylethylketone, a lower alkanol, e.g. methanol or ethanol, dioxan, acetonitrile or an aromatic hydrocarbon, e.g. toluene, at a temperature between 0° C. and 150° C. and preferably at between 10° C. and 60° C.

The reaction is preferably carried out in the presence of an excess of the isothiocyanate of formula II.

The isothiocyanates of general formula II may be prepared by the reaction of an ester of the general formula:

$$XCO_2R \qquad\qquad IV$$

(wherein R is as hereinbefore defined and X is a bromine, iodine or, preferably, chlorine atom) and a thiocyanate of the general formula:

$$(NCS)_qM \qquad\qquad V$$

(wherein M is a metal, preferably an alkali metal or an alkaline earth metal, atom and $q$ is the valency of that metal). The reaction may be carried out in the presence of an inert organic solvent, for example a lower alkanone, e.g. acetone, or acetonitrile, at a temperature between 0° C. and 100° C., and preferably between 20° C. and 50° C.

The preparation of compounds of formula II may be effected in situ for subsequent reaction with compounds of formula III or, if desired, the compounds of formula II may be isolated by known methods prior to reaction with compounds of formula III. 2. by reaction of a compound of the general formula:

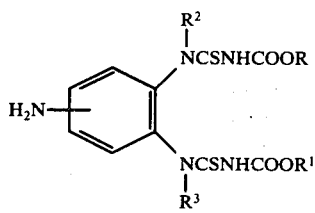

VI (wherein R,R¹,R² and R³ are as hereinbefore defined) with an acid halide, e.g. chloride, or anhydride of an alkanoic acid containing 2 to 4 carbon atoms and which may optionally be substituted by a cycloalkyl group containing from 3 to 6 carbon atoms, an acid halide, e.g. chloride or anhydride of a cycloalkane carboxylic acid containing from 3 to 6 carbon atoms in the cycloalkane moiety, or with an alkyl haloformate, e.g. a chloroformate, containing 2 to 4 carbon atoms and wherein the alkyl moiety may be straight- or branched-chain, to give compounds of general formula I wherein R⁴ represents an alkanoylamino, cycloalkylcarbonamide or alkoxycarbonylamido group. The reaction is preferably carried out in an inert organic solvent, for example a lower alkanone, e.g. acetone, in the presence of a basic condensing agent, for example an alkali metal (e.g. sodium) bicarbonate, at a temperature between 20° C. and 100° C. and preferably at the reflux temperature of the reaction mixture.

Compounds of general formula III, wherein R² represents a hydrogen atom and R⁴ and Y are as hereinbefore defined, may be prepared by the reduction of compounds of the general formula:

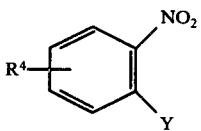

VII (wherein R⁴ and Y are as hereinbefore defined)

a. when Y is a group —N(R³)CSNHCOOR¹, by known methods for the reduction of an aromatic nitro group in compounds containing sulphur under neutral or acidic conditions, for example with ferrous chloride, ferrous hydroxide, stannous chloride, reduced iron powder or iron pin dust, if desired in the presence of an inorganic acid, e.g. hydrochloric acid. Reduction may be carried out in an aqueous-organic inert solvent medium, for example an aqueous lower alkanol, e.g. aqueous methanol, or aqueous ethanol, or an aqueous lower alkanone, e.g. aqueous acetone, at a temperature between 20° C. and the reflux temperature of the reaction mixture. Reduction with reduced iron powder may, if desired, be carried out in the presence of an inorganic chloride, for example ammonium chloride, magnesium chloride or ferric chloride. or b. when Y is a primary amino or monomethylamine group, by known methods for the reduction of aromatic nitro groups, for example by hydrogenation in the presence of a hydrogenation catalyst, e.g. platinum, or by the use of ferrous chloride and reduced iron powder.

Compounds of general formula VI may be prepared by the reduction of compounds of the general formula:

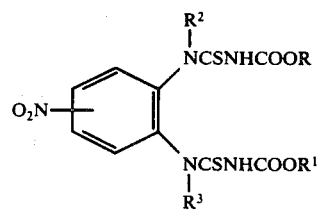

VIII (wherein the various symbols are as hereinbefore defined) by the procedure hereinbefore described for the reduction of compounds of general formula VII by known methods for the reduction of an aromatic nitro group in compounds containing sulphur.

Compounds of general formula VIII may be prepared by the application to nitro-substituted-o-phenylenediamines of methods hereinbefore described for the conversion of a primary amino group to groups —N(R²)CSNHCOOR and —N(R³)CSNHCOOR¹.

By the term 'known methods' as used in the present specification is meant methods heretofore used or described in the chemical literature.

For example, compounds hereinbefore described may be prepared by the following Procedure.

Procedure

Potassium thiocyanate (54.4 g; 0.56 mole), ethyl chloroformate (51.0 g; 0.54 mole) and dry acetone (300 ml) were mixed with stirring at laboratory temperature. The temperature of the reaction mixture rose spontaneously to 51° C. and stirring was continued for two hours at 45° C. to 51° C. The reaction mixture was then cooled in an ice-bath to a temperature of 15° C. and o-phenylenediamine (15.4 g; 0.143 mole) was then added in portions, with stirring, over a period of fifteen minutes, the temperature of the stirred reaction mixture being maintained at between 15° C. and 20° C. during the addition. When the addition was complete, the reaction mixture was stirred at laboratory temperature for eighteen hours and then filtered. The solid residue was washed with water and dried in a vacuum desiccator to give a crude product (41.6 g), m.p. 179°–180° C. (with decomposition). A portion (8 g) of this crude product was recrystallised from dry methanol (400 ml) to give 1,2-bis-(3-methoxycarbonyl-2-thioureido)benzene (6.5 g), m.p. 198°–200° C. (with decomposition).

1,2-Bis-(3-ethoxycarbonyl-2-thioureido)benzene, m.p. 194°–196° C., may be prepared in a similar manner, replacing the methyl chloroformate by ethyl chloroformate.

It is known, for example from British Patent No. 1191406 granted to Nippon Soda Company Limited on an application filed 11th October 1968 that compounds of general formula I, wherein R and R¹ each represent an unsubstituted alkyl group containing from 1 to 12 carbon atoms, an alkyl group containing 1 or 2 carbon atoms substituted by a halogen atom or a methoxy or phenyl group, an alkenyl or alkynyl group containing 2 to 3 carbon atoms or an aryl group optionally substituted by a halogen atom or a nitro or methyl group, R² and R³ each represent a hydrogen atom or a methyl group, R⁴ represents a hydrogen or halogen atom or a nitro or methyl group, and their metal complexes, possess fungicidal properties. There is no mention in the patent that the benzene derivatives possess anthelmintic or anti-viral activity.

The present invention therefore includes within its scope, as new and useful compounds, those benzene derivatives of general formula I wherein R, $R^1$, $R^2$, $R^3$ and $R^4$ are as defined in relation to that formula, with the proviso that when R and $R^1$ are alkyl groups containing not more than 4 carbon atoms or alkyl groups of 1 to 2 carbon atoms substituted by a halogen atom or methoxy group, or alkenyl or alkynyl groups of 2 or 3 carbon atoms, $R^4$ is other than a hydrogen or halogen atom or a methyl group. For convenience in referring hereinafter to these new compounds of the invention they will be identified as a class by reference to general formula IX although no formula will actually be depicted.

A group of compounds within the invention are those of general formula I wherein $R^4$ is a straight- or branched-chain alkyl group containing 2 to 4 carbon atoms, e.g. n-butyl, a straight- or branched-chain alkanoylamino group containing 1 to 4 carbon atoms, e.g. acetamido, a straight- or branched-chain alkoxycarbonylamino group, e.g. methoxycarbonylamino or isopropoxycarbonylamino, a straight- or branched-chain alkanoyl group containing 2 to 4 carbon atoms, e.g. acetyl, or a benzoyl group and R and $R^1$ each represent a straight- or branched-chain aliphatic hydrocarbon group containing not more than 4 carbon atoms, e.g. methyl or ethyl.

Also included with this invention, as new compounds, are 4-fluoro-1,2-bis-(3-methoxycarbonyl-2-thioureido)-benzene and 4-fluoro-1,2-bis-(3-ethoxycarbonyl-2-thioureido)benzene.

In addition to possessing anthelmintic and anti-viral activity, the new compounds of general formula IX are also useful as agricultural pesticides, in particular as fungicides against species of fungi which are pathogenic to plants, and also active as fungicides against fungal species which are pathogenic to animals, in particular *Trichophyton mentagrophytes.*

As fungicides for use against species of fungi pathogenic to plants, the new compounds of general formula IX, e.g. 1,2-bis-(3-allyloxycarbonyl-2-thioureido)benzene, are particularly useful in the control of *Alternaria solani, Betrytis cinerea, Cercopora beticola, Cladosporium fulvum, Collectotrichum lagenarium, Corynespora melongenae, Elsinoe fawcetti, Erysiphe graminis, Fusarium sambucinum, Glomerella cingulata,* Helminthosporium spp., e.g. H. signoideum and H. avenae, Mycosphaerella spp., e.g. M pomi and M. pinodes, *Pellicularia sasaki,* Penicillium spp., *Phaeoisariopsis vitis, Piricularia oryzae, Podosphaerea leucotricha, Pseudoperonospora humuli,* Sclerotinia spp., e.g. S. cinerea and S. sclerotiorum, Sphaerotheca spp., e.g. S. fuliginea and S. humuli and *Venturia inaequalis.*

The new compounds of general formula IX may be used as fungicides against fungi pathogenic to plants in the form of fungicidal compositions, suitable for use in agriculture, containing as active ingredient at least one of the benzene derivatives of general formula IX in association with one or more diluents compatible with the benzene derivatives and suitable for use in fungicidal compositions. Preferably the compositions contain between 0.005% and 95% by weight of the compounds of general formula IX. Suitable solid diluents include aluminium silicate, kieselguhr, tricalcium phosphate, powdered cork, adsorbent carbon black, magnesium silicate, a clay such as kaolin, bentonite or attapulgite, or a compatible solid wetting, dispersing or emulsifying agent. The compositions containing solid diluents, which may take the form of dusts or wettable powders, are prepared by impregnating the solid diluents with solutions of the compounds of general formula IX in volatile solvents and evaporating the solvents, or by injecting those compounds of general formula IX are viscous liquids at room temperature, under high pressure into a suitable powder-blender containing the solid diluent or diluents, and, if necessary, grinding the products so as to powders.

The wetting, dispersing and emulsifying agents which may be present, particularly in wettable powders, may be of the ionic or non-ionic types, for example, sulphoricinoleates, quaternary ammonium derivatives or products based upon condensates of ethylene oxide with nonyl and octyl phenol, or fatty acid esters of anhydrosorbitols which have been rendered soluble by etherification of the free hydroxy groups by condensation with ethylene oxide, or mixtures of these types of agents. Wettable powders according to the present invention may be treated with water immediately before use to give suspensions ready for application.

Liquid compositions may take the form of solutions, suspensions and emulsions of the compounds of general formula IX which may, if desired, incorporate wetting, dispersing or emulsifying agents. These emulsions, suspensions and solutions may be prepared using aqueous, organic or aqueous-organic diluents, for example acetophenone, isophorone, toluene, xylene and mineral, animal or vegetable oils (and mixtures of these diluents), which may contain wetting, dispersing or emulsifying agents to the ionic or non-ionic types of mixtures thereof, for example those of the types described above. When desired, the emulsions containing the compounds of general formula IX may be used in the form of self-emulsifying concentrates containing the active substances dissolved in the emulsifying agents or in solvents containing emulsifying agents compatible with the active substance, the simple addition of water to such concentrates producing compositions ready for use. Fungicidal compositions in the form of aerosols containing the compounds of general formula IX are also within the scope of the present invention. If desired, the fungicidal compositions according to the present invention may contain other adjuvants such as adhesives.

Accordingly, there is provided a method for the destruction of fungi pathogenic to plants which comprises the application of the fungicidal compositions comprising compounds of general formula IX, if necessary after suitable dilution, to crop-growing areas infested with these fungi. By the term 'crop-growing area' is meant areas in which economically valuable crops are growing. Preferably the fungicidal compositions are applied at rates of from 0.5 to 3 lbs. of benzene derivatives per acre, more particularly in the form of aqueous sprays prepared by diluting concentrates with water.

The new compounds of general formula IX may be used as fungicides against fungi pathogenic to animals in the form of therapeutically useful compositions comprising at least one of the compounds in association with a pharmaceutically-acceptable carrier or coating of the type hereinbefore described as suitable for the use of compounds of general formula I as anthelmintics and anti-viral agents. Therapeutically useful compositions comprising at least one of the new compounds of general formula IX for use against fungi pathogenic to animals may be formulations suitable for topical application, e.g. lotions, ointments or creams.

The following Examples illustrate the preparation of new compounds according to the present invention:

EXAMPLE 1

Potassium thiocyanate (28.5 g, 0.29 mole), methyl chloroformate (27.5 g, 0.29 mole) and dry acetone (150 ml) were mixed with stirring at laboratory temperature. The temperature of the reaction mixture rose spontaneously to 40° C. and stirring was continued for two hours at that temperature. The reaction mixture was then cooled in an ice-bath to a temperature of 15° C. and treated with a solution of the 4-n-butyl-1,2-phenylenediamine, prepared as hereinafter described, in dry acetone (20 ml), dropwise with stirring, over a period of fifteen minutes, the temperature being maintained at between 15° C. and 20° C. during the addition. When the addition was complete, the reaction mixture was stirred at laboratory temperature for eighteen hours and then filtered. The solid residue was stirred with water (100 ml), refiltered and dried in a vacuum dessicator to give a crude product (1.2 g). The filtrate was concentrated to small bulk, and the solid which precipitated was filtered off. This was washed with water and dried to give a further quantity of crude product (28 g). The combined crude products were recrystallised from methanol (320 ml) to give 1,2-bis-(3-methoxycarbonyl-2-thioureido)-4-n-butylbenzene (11.5 g), m.p. 170°–171° C. (with decomposition). The 4-n-butyl-1,2-phenylenediamine used as a starting material may be prepared in the following manner:

4-n-Butyl-2-nitroaniline (12.5 g, 0.065 mole), platinum oxide (0.75 g) and ethanol (125 ml) were mixed together and shaken in an atmosphere of hydrogen at atmospheric pressure and laboratory temperature. After six hours 5.2 liters of hydrogen had been absorbed. The mixture was filtered and ethanol removed from the filtrate by distillation. Benzene (40 ml) was added to the residual oil and this was then also removed by distillation. The crude 4-n-butyl-1,2-phenylenediamine thus obtained was used directly in the preparation of 1,2-bis-(3-methoxycarbonyl-2-thioureiddo)-4-n-butylbenzene.

In a similar manner, substituting an equimolar quantity of ethyl chloroformate for the methyl chloroformate there was prepared 1,2-bis-(3-ethoxycarbonyl-2-thioureido)-4-n-butylbenzene, m.p. 175°–176° C. (with decomposition).

By again proceeding in a similar manner substituting the appropriate quantity of 1,2-diamino-4-isopropoxycarbonylaminobenzene for the 4-butyl-1,2-phenylenediamine, there was obtained 1,2-bis-(3-methoxycarbonyl-2-thioureido)-4-isopropoxycarbonylaminobenzene, m.p. 196°–7° C. (with decomposition).

The 1,2-diamino-4-isopropoxycarbonylaminobenzene used as starting material was prepared in the following manner:

A mixture of a solution of 2-nitro-4-isopropoxycarbonylaminoaniline (17.9 g, 0.075 mole) in methanol (450 ml) and platinum oxide (1.0 g) was shaken in an atmosphere of hydrogen at atmospheric pressure and laboratory temperature for several hours, during which time 5.04 liters of hydrogen were absorbed. The mixture was filtered, and the methanol removed in vacuo and the dark solid residue recrystallised from benzene to give 1,2-diamino-4-isopropoxycarbonylaminobenzene (10.4 g), m.p. 108°–110° C.

EXAMPLE 2

Dry potassium thiocyanate (42.8 g), methyl chloroformate (37.8 g) and dry acetonitrile (240 ml) were mixed with stirring at laboratory temperature and stirring was continued for 1 hour at 40°–45° C. The mixture was then cooled in an ice-bath to 15° C. and 4-fluoro-o-phenylenediamine (12.6 g) was added in portions during 10 minutes, the temperature of the reaction mixture being maintained between 15° and 20° C. during the addition. When the addition was complete the mixture was stirred at 30°–40° C. temperature for 2 hours, poured into water (1 liter) and the brown-red solid which separated was filtered off and washed with water.

The crude product was recrystallised from methanol to give 4-fluoro-1,2-bis-(3-methoxycarbonyl-2-thioureido)benzene (14.6 g), m.p. 183°–185° C. (with decomposition).

i. By proceeding in a similar manner but substituting the appropriate quantities of 4-acetyl-o-phenylenediamine, 4-benzoyl-o-phenylenediamine, 4-methoxycarbonylamino-o-phenylenediamine and 4-acetamido-o-phenylenediamine for the 4-fluoro-o-phenylenediamine, there were obtained 3,4-bis-(3-methoxycarbonyl-2-thioureido)acetophenone, m.p. 202°–203° C. (with decomposition), 3,4-bis-(3-methoxycarbonyl-2-thioureido)benzophenone, m.p. 187°–188° C. (with decomposition), 4-methoxycarbonylamino-1,2-bis-(3-methoxycarbonyl-2-thioureido)-benzene, m.p. 148°–150° C. (with decomposition), and 4-acetamido-1,2-bis-(3-methoxycarbonyl-2-thioureido)benzene, m.p. 183°–185° C. (with decomposition), respectively. ii. By proceeding in a similar manner, but substituting the appropriate quantity of ethyl chloroformate for the methyl chloroformate there was obtained 4-fluoro-1,2-bis-(3-ethoxycarbonyl-2-thioureido)benzene, m.p. 191°–193° C. (with decomposition).

EXAMPLE 3

Acetyl chloride (1.66 g; 0.0212 mole) was added dropwise during five minutes to a stirred suspension of 3,4-bis-(3-methoxycarbonyl-2-thioureido)aniline (4.0 g; 0.0112 mole) and sodium bicarbonate (1.78 g; 0.0212 mole) in dry acetone (50 ml). The temperature of the reaction mixture rose spontaneously to 30° C. After completion of the addition, the mixture was refluxed with stirring for 6 hours, cooled and poured into water. The solid which separated was filtered off, washed well with water and crystallised from ethanol to give 4-acetamido-1,2-bis-(3-methoxycarbonyl-2-thioureido)-benzene, m.p. 183°–185° C. (with decomposition).

By proceeding in a similar manner but substituting the appropriate quantity of methyl chloroformate for the acetyl chloride, there was obtained 1,2-bis-(3-methoxycarbonyl-2-thioureido)-4-methoxycarbonylaminobenzene, m.p. 148°–150° C. (with decomposition).

3,4-Bis-(3-methoxycarbonyl-2-thioureido)aniline, used as starting material in the above preparation, was prepared as follows:

Methyl chloroformate (113.4 g; 1.20 mole) was added dropwise to a stirred suspension of potassium thiocyanate (128 g; 1.32 mole) in dry acetonitrile (450 ml). The temperature of the reaction mixture rose spontaneously to 35° 1 C. and stirring was continued for two hours at 30° C. to 40° C. The reaction mixture was then cooled to 25° C. and 4-nitro-o-phenylenediamine (45.9 g; 0.30 mole) was added in portions, with stirring, during thirty minutes. The temperature of the reaction mixture rose spontaneously to 35° C. Stirring was continued for a further three hours at 30° C. to 40° C., and then the reaction mixture was poured into water (3 liters). The solid which separated was filtered off, washed well with water, and recrystallised from acetonitrile to give crude 1,2-bis-(3-methoxycarbonyl-2-thioureido)-4-nitrobenzene (93.7 g), m.p. 169°–171° C (with decomposition) which was pure enough to use in the next stage of the preparation. [A portion (4.0 g) of this crude product was recrystallised from acetonitrile to give 1,2-bis-(3-methoxycarbonyl-2-thioureido)-4-nitrobenzene (3.1 g), m.p. 174°–176° C. (with decomposition)].

1,2-Bis-(3-methoxycarbonyl-2-thioureido)-4-nitrobenzene (9.7 g; 0.025 mole) and ferrous chloride tetrahydrate (1.13 g) were finely powdered together and suspended in a mixture of methanol (110 ml) and water (10 ml). The vigorously stirred suspension was then heated to reflux and reduced iron powder (6.53 g) was added in portions during five minutes. When the addition was complete, the reaction mixture was refluxed for a further forty five minutes and filtered. The dark brown filter cake was extracted with boiling methanol (2 × 120 ml), and the hot methanol solutions were combined with the hot aqueous methanol filtrate and evaporated to 200 ml. The solution was cooled to room temperature and the solid which separated was filtered off to give 3,4-bis-(3-methoxycarbonyl-2-thioureido)aniline (4.70 g), m.p. 186–187° C. (with decomposition), in the form of off-white crystals.

The 2-nitro-4-isopropoxycarbonylaminoaniline referred to in Example I was prepared as follows:

A stirred suspension of 2,5-diaminonitrobenzene (60 g.) in a solution of sodium bicarbonate (49.4 g) in water (780 ml) at 10° C. was treated dropwise with isopropyl chloroformate (48 g) and the mixture was stirred at room temperature for 3 hours. The crude brown solid was filtered off, washed well with water and dried to give 4-isopropoxycarbonylamino-2-nitroaniline (90.0 g), m.p. 158°–160° C., which was used in the next stage of the synthesis without further purification being necessary. Recrystallisation of a sample from toluene gave pure 2-nitro-4-isopropoxycarbonylaminoaniline, m.p. 161°–163° C.

Other compounds of general formula I which may be obtained by the procedures described in the foregoing Examples are: 3,4-bis-(3-methoxycarbonyl-2-thioureido)toluene, m.p. 190° C., 2,3-bis-(3-methoxycarbonyl-2-thioureido)toluene, m.p. 195°–196° C., 4-chloro-1,2-bis-(3-ethoxycarbonyl-2-thioureido)benzene, m.p. 178°–180° C., 1-(3-ethoxycarbonyl-1-methyl-2-thioureido)-2-(3-ethoxycarbonyl-2-thioureido)benzene, m.p. 173°–175° C., 1-(3-methoxycarbonyl-2-thioureido)-2-(3-ethoxycarbonyl-2-thioureido)benzene, m.p. 178°–179° C., 1,2-bis-(3-allyloxycarbonyl-2-thioureido)benzene, m.p. 214°–215° C., 1,2-bis-(3-allyloxycarbonyl-2-thioureido)benzene, m.p. 164°–165° C., and 1,2-bis-(3-propargyloxycarbonyl-2-thioureido)benzene, m.p. 167°–168° C.

All the above-mentioned melting points were with decomposition of the specified product except for the third.

The following Examples illustrate the formulation of therapeutically useful compositions including benzene derivatives of general formula I.

EXAMPLE 4

Tablets of the formula:

| | |
|---|---|
| 1,2-bis-(3-methoxycarbonyl-2-thioureido)-benzene | 250 mg. |
| lactose | 200 mg. |
| starch | 50 mg. |
| polyoxyethylene sorbitan monolaurate | 0.5 mg. |
| magnesium stearate | 5 mg. | are prepared by mixing the benzene derivative and the lactose with part of the starch and granulating with a 5% starch mucilage containing the polyoxyethylene sorbitan monolaurate.

The mixture is sifted through a 20 mesh British Standard sieve, dried, and the remainder of the starch, together with the magnesium stearate, is incorporated into the mixture. After a second sifting through a 20 mesh British Standard sieve the mixture is compressed into tablets.

EXAMPLE 5

A wettable powder was made up from the following components:

| | |
|---|---|
| 1,2-bis-(3-methoxycarbonyl-2-thioureido)benzene | 75% w/w |
| diatomaceous earth | 15% w/w |
| micronised silica | 2% w/w |
| wetting agent (blend of polyoxyethylene alkyl ethers, polyoxyethylene fatty acids and their esters | 8% w/w | by mixing the components and milling them in an air-jet miller.

The resultant wettable powder was made up in a 70% dispersion in water for administration to sheep, e.g. in the experiments hereinbefore described.

EXAMPLE 6

A wettable powder was made up from the following components:

| | |
|---|---|
| 1,2-bis-(3-ethoxycarbonyl-2-thioureido)benzene | 52% w/w |
| finely-divided synthetic magnesium silicate | 39% w/w |
| micronised silica | 2% w/w |
| wetting agent (blend of polyoxyethylene alkyl ethers, polyoxyethylene fatty acids and their esters) | 7% w/w |

By mixing the components and milling them in an air-jet miller.

The resultant wettable powder was made up in a 50% dispersion in water for administration to sheep, e.g. in the experiments hereinbefore described.

EXAMPLE 7

1,2-Bis-(3-methoxycarbonyl-2-thioureido)benzene (1 g), previously sifted through a 40 mesh British Standard sieve, is packed into a gelatin capsule.

The 1,2-bis-(3-methoxycarbonyl-2-thioureido)benzene may be replaced by the same quantity of any other compound of general formula I, e.g. 1,2-bis-(3-ethoxycarbonyl-2-thioureido)benzene.

EXAMPLE 8

A preparation for oral administration is obtained by mixing 1,2-bis-(3-methoxycarbonyl-2-thioureido)benzene (1 g), previously sifted through a 40 mesh British Standard sieve, and polyethylene glycol 6000 (10 g) at 50° C., and cooling to 25° C. to obtain a gel.

The 1,2-bis-(3-methoxycarbonyl-2-thioureido)benzene may be replaced by a similar quantity of any other compound of general formula I, e.g. 1,2-bis-(3-ethoxycarbonyl-2-thioureido)benzene.

EXAMPLE 9

1,2-Bis-(3-methoxycarbonyl-2-thioureido)benzene (18 parts by weight) is added to wheat middlings (82 parts by weight) and intimately mixed to give a concentrate suitable for incorporation in an animal feedstuff at a rate sufficient to give an anthelmintically-effective amount of the benzene derivative in the feedstuff consumed by the animal. If desired, conventional adhesive agents may be incorporated into the concentrate which may then be compressed into pellets. The pellets may be fed to animals at a rate sufficient to administer an anthelmintically-effective amount of the benzene derivative to the animal, if desired mixed with an animal feedstuff.

The 1,2-bis-(3-methoxycarbonyl-2-thioureido)benzene may be replaced by a similar quantity of any other compound of general formula, I, e.g. 1,2-bis-(3-ethoxycarbonyl-2-thioureido)benzene.

EXAMPLE 10

1,2-Bis-(3-methoxycarbonyl-2-thioureido)benzene (5 parts by weight) was added to limestone flour (20 parts by weight). The mixture was ground to give a concentrate suitable for incorporation in an animal feedstuff at a rate sufficient to give an anthelmintically-effective amount of the benzene derivative in the feedstuff consumed by the animal.

The 1,2-bis-(3-methoxycarbonyl-2-thioureido)benzene may be replaced by a similar quantity of any other compound of general formula I, e.g. 1,2-bis-(3-ethoxycarbonyl-2-thioureido)benzene.

EXAMPLE 11

A suspension for oral administration for use as an anthelmintic is obtained by mixing diethylcarbamazine citrate (4.4 g; prepared as described in U.S. Pat. No. 2,467,895) and 1,2-bis-(3-ethoxycarbonyl-2-thioureido)-benzene (19.6 g of a 52% w/w wettable powder prepared as described in Example 6) with water (140 ml).

EXAMPLE 12

A suspension for oral administration for use as an anthelmintic is obtained by mixing 1-styrylpyridinium amsonate monhydrate (10 g; prepared as described in British Patent No. 1,221,061), previously sifted through a 60 mesh British Standard sieve, and 1,2-bis-(3-ethoxycarbonyl-2-thioureido)benzene (19.6 g of a 52% w/w wettable powder prepared as described in Example 6) with water (140 ml).

We claim:

1. A method for the treatment of helminth infections in man and domestic animals which comprises administering to man or a domestic animal infected with helminths an anthelmintically effective amount of at least one benzene derivative of the formula:

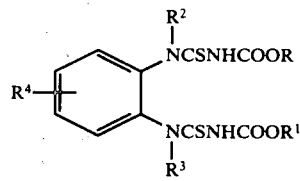

wherein R and $R^1$ each represent an aliphatic hydrocarbon group of 1 to 4 carbon atoms which is unsubstituted or substituted by halogen or alkoxy of 1 to 4 carbon atoms, $R^2$ and $R^3$ each represent hydrogen or methyl, and $R^4$ represents hydrogen, halogen, alkyl of 1 to 4 carbon atoms, alkanoylamino of 1 to 4 carbon atoms which is unsubstituted or substituted by cycloalkyl of 3 to 6 carbon atoms, alkoxycarbonylamino of 2 to 4 carbon atoms, alkanoyl of 2 to 4 carbon atoms, benzoyl or N-methylmethanesulphonylamino.

2. A method according to claim 1 in which man or the domestic animal is infected with parasitic nematode worms.

3. A method according to claim 1 in which R and $R^1$ each represent methyl, ethyl, allyl or propargyl.

4. A method according to claim 1 in which R and $R^1$ both represent methyl groups or ethyl groups.

5. A method according to claim 1 in which R and $R^1$ both represent methyl groups or ethyl groups and $R^2$ and $R^3$ both represent hydrogen.

6. A method according to claim 1 in which $R^4$ represents hydrogen.

7. A method according to claim 1 in which R and $R^1$ both represent methyl groups or ethyl groups, and $R^2$, $R^3$ and $R^4$ represent hydrogen.

8. A method according to claim 1 in which the dose of benzene derivative administered to man or domestic animal is 5 mg. to 1000 mg. per kilogram of body weight.

9. A method according to claim 8 in which the dose of benzene derivative administered to man or domestic animal is 25 mg. to 250 mg. per kilogramme of body weight.

10. A method according to claim 1 in which the domestic animals treated are cattle, sheep, pigs, goats, poultry or equines.

11. A method according to claim 1 in which R and $R^1$ both represent ethyl and $R^2$, $R^3$ and $R^4$ represent hydrogen.

12. Medicated animal feedstuffs comprising an animal feedstuff and 0.001% to 3% by weight of said feedstuff of a benzene derivative of the formula:

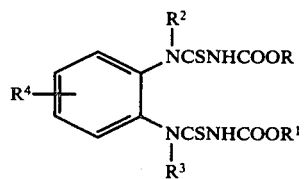

wherein R and $R^1$ each represent an aliphatic hydrocarbon group of 1 to 4 carbon atoms which is unsubstituted or substituted by halogen or alkoxy of 1 to 4 carbon atoms, $R^2$ and $R^3$ each represent hydrogen or methyl, and $R^4$ represents hydrogen, halogen, alkyl of 1 to 4 carbon atoms, alkanoylamino of 1 to 4 carbon atoms which is unsubstituted or substituted by cycloalkyl of 3 to 6 carbon atoms, alkoxycarbonylamino or 2 to 4 carbon atoms, alkanoyl of 2 to 4 carbon atoms, benzoyl or N-methylmethanesulphonylamino.

13. Medicated animal feedstuffs according to claim 12 which include, as auxiliary therapeutic agent, a fasciolicide or anthelmintic.

14. A method for the treatment of helminth infections in man and domestic animals which comprises administering to man or a domestic animal infected with helminths an anthelmintically effective amount of at least one benzene derivative of the formula:

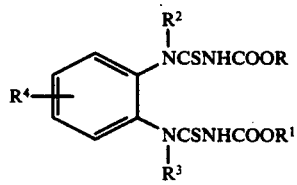

wherein R and R¹ each represent an aliphatic hydrocarbon of 1 to 4 carbon atoms which is unsubstituted or substituted by halogen or alkoxy of 1 to 4 carbon atoms, R² and R³ each represent hydrogen or methyl, and R⁴ represents hydrogen, halogen or alkyl of 1 to 4 carbon atoms.

15. A method of controlling helminths in sheep which comprises the oral administration to sheep in need of such control an anthelmintically effective amount of a compound corresponding to the following formula:

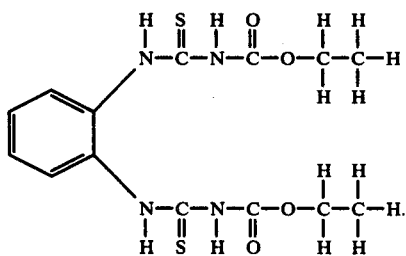

* * * * *